US008403755B2

(12) United States Patent
Kerr

(10) Patent No.: US 8,403,755 B2
(45) Date of Patent: Mar. 26, 2013

(54) BIOMETRIC BROADBAND GAMING SYSTEM AND METHOD

(75) Inventor: Michael A. Kerr, Carson City, NV (US)

(73) Assignee: NexRf, Corp., Reno, NV (US)

( * ) Notice: Subject to any disclaimer, the term of this patent is extended or adjusted under 35 U.S.C. 154(b) by 527 days.

(21) Appl. No.: 10/681,034

(22) Filed: Oct. 8, 2003

(65) Prior Publication Data

US 2005/0043096 A1 Feb. 24, 2005
US 2009/0325708 A9 Dec. 31, 2009

Related U.S. Application Data

(63) Continuation of application No. 09/899,559, filed on Jul. 5, 2001, now abandoned.

(60) Provisional application No. 60/266,956, filed on Feb. 6, 2001.

(51) Int. Cl.
*A63F 9/24* (2006.01)
*A63F 13/00* (2006.01)
*G06F 17/00* (2006.01)
*G06F 19/00* (2006.01)

(52) U.S. Cl. ............... 463/42; 463/17; 463/25; 705/44; 380/251

(58) Field of Classification Search ............... None
See application file for complete search history.

(56) References Cited

U.S. PATENT DOCUMENTS

| | | | |
|---|---|---|---|
| 4,339,798 A | 7/1982 | Hedges et al. | |
| 4,856,787 A | 8/1989 | Itkis | |
| 5,586,937 A | 12/1996 | Menashe | |
| 5,594,491 A | 1/1997 | Hodge et al. | |
| 5,630,757 A | 5/1997 | Gagin et al. | |
| 5,643,086 A | 7/1997 | Alcorn et al. | |
| 5,738,583 A | 4/1998 | Comas et al. | |
| 5,761,416 A | 6/1998 | Mandal et al. | |
| 5,762,552 A | 6/1998 | Vuong et al. | |
| 5,768,382 A * | 6/1998 | Schneier et al. | 380/251 |
| 5,779,545 A | 7/1998 | Berg et al. | |
| 5,800,268 A | 9/1998 | Molnick | |
| 5,851,149 A * | 12/1998 | Xidos et al. | 463/42 |
| 5,871,398 A * | 2/1999 | Schneier et al. | 463/16 |
| 5,902,983 A | 5/1999 | Crevelt et al. | |
| 6,001,016 A * | 12/1999 | Walker et al. | 463/42 |
| 6,010,404 A | 1/2000 | Walker et al. | |
| 6,106,396 A | 8/2000 | Alcorn et al. | |
| 6,142,876 A | 11/2000 | Cumbers | |
| 6,178,510 B1 * | 1/2001 | O'Connor et al. | 726/5 |
| 6,409,602 B1 | 6/2002 | Wiltshire et al. | |
| 6,500,068 B2 | 12/2002 | Walker et al. | |
| 6,508,709 B1 * | 1/2003 | Karmarkar | 463/42 |
| 6,508,710 B1 * | 1/2003 | Paravia et al. | 463/42 |
| 6,527,638 B1 * | 3/2003 | Walker et al. | 463/25 |

(Continued)

OTHER PUBLICATIONS

Wireless Network as downloaded from wikipedia.com, pages. 5 pages.*

(Continued)

*Primary Examiner* — Paul A D'Agostino
(74) *Attorney, Agent, or Firm* — Michael A. Kerr; Kerr IP Group, LLC

(57) ABSTRACT

A wireless broadband gaming system and method is described. The wireless broadband gaming system includes a wireless network access device and a gaming system. The gaming system includes a registration database, a verification system, a video server and a gaming server. The video server stores images corresponding to at least one particular game outcome. The gaming server generates a random game output that associates the random game output with at least one particular game outcome. The gaming server communicates the images corresponding to the particular game outcome to the wireless network access device after verifying the wireless network device is a secure device and after verifying the user has registered.

22 Claims, 9 Drawing Sheets

U.S. PATENT DOCUMENTS

| | | | |
|---|---|---|---|
| 6,575,834 B1* | 6/2003 | Lindo | 463/40 |
| 6,612,928 B1* | 9/2003 | Bradford et al. | 463/29 |
| 6,628,939 B2 | 9/2003 | Paulsen | |
| 6,638,170 B1* | 10/2003 | Crumby | 463/42 |
| 6,676,522 B2 | 1/2004 | Rowe | |
| 6,682,421 B1* | 1/2004 | Rowe et al. | 463/25 |
| 6,702,672 B1* | 3/2004 | Angell et al. | 463/25 |
| 6,709,333 B1* | 3/2004 | Bradford et al. | 463/29 |
| 6,709,631 B2* | 3/2004 | Mori et al. | 422/53 |
| 6,719,631 B1* | 4/2004 | Tulley et al. | 463/17 |
| 6,749,512 B2 | 6/2004 | MacGregor et al. | |
| 6,875,110 B1* | 4/2005 | Crumby | 463/42 |
| 6,884,162 B2 | 4/2005 | Raverdy et al. | |
| 6,942,574 B1 | 9/2005 | LeMay et al. | |
| 7,107,245 B1* | 9/2006 | Kowalick | 705/44 |
| 7,338,372 B2 | 3/2008 | Morrow et al. | |
| 7,341,522 B2 | 3/2008 | Yamagishi | |
| 7,534,169 B2 | 5/2009 | Amaitis et al. | |
| 7,611,407 B1 | 11/2009 | Itkis et al. | |
| 2001/0004768 A1 | 6/2001 | Hodge et al. | |
| 2001/0005908 A1 | 6/2001 | Hodge et al. | |
| 2002/0007494 A1 | 1/2002 | Hodge | |
| 2002/0056125 A1 | 5/2002 | Hodge et al. | |
| 2002/0056143 A1 | 5/2002 | Hodge et al. | |
| 2002/0077167 A1* | 6/2002 | Merari | 463/13 |
| 2002/0103028 A1* | 8/2002 | Carter et al. | 463/42 |
| 2002/0142844 A1 | 10/2002 | Kerr | |
| 2006/0189382 A1 | 8/2006 | Muir et al. | |
| 2008/0097858 A1 | 4/2008 | Vucina et al. | |

OTHER PUBLICATIONS

HTTP Cookie, redirected from tracking cookie as downloaded from wikipedia, 41 pages.*

Interactive Gambling Industry Code, Dec. 2001, 7 pages.*

* cited by examiner

_70

| REGISTRATION DATA FIELDS ||
|---|---|
| NAME | BIOMETRIC |
| ADDRESS | PLAYER ID |
| USER NAME | MAC ID |
| PASSWORD | IP ADDRESS |
| CREDIT CARD | BROWSER |
| DATE | COOKIES |
| TIME | CRYPTO KEYS |

_72

| USER SUBMITTED DATA ||
|---|---|
| NAME | BIOMETRIC |
| ADDRESS | PLAYER ID |
| USER NAME | MAC ID |
| PASSWORD | IP ADDRESS |
| CREDIT CARD | BROWSER |
| DATE | COOKIES |
| TIME | CRYPTO KEYS |

| PLAYER DATA FIELDS ||
|---|---|
| PLAYER ID | SESSION TIME FOR TYPE OF GAME |
| DATE | AMOUNT PLAYED DURING SESSION |
| TIME IN | CREDIT CARD INFORMATION |
| TIME OUT | TRANSACTION REQUEST |
| TYPE GAME | TRANSACTION APPROVAL |
| CREDITS IN | TRANSFER OF CREDITS |
| CREDITS OUT | TRANSFER TO PLAYER CREDIT CRD |
| BONUS | CRYPTO KEYS |

FIG. 6

BIOMETRIC BROADBAND GAMING SYSTEM AND METHOD

CROSS REFERENCES TO RELATED APPLICATIONS

This patent application is a continuation of patent application Ser. No. 09/899,559 having a filing date of Jul. 5, 2001, now abandoned, which claims the benefit of provisional patent application 60/266,956 filed Feb. 6, 2001.

BACKGROUND

1. Field

The present invention is a wireless broadband interactive gaming system and method. More particularly, the wireless broadband interactive gaming system and method operates in a networked environment that interfaces with a gaming server and a video server.

2. Description of Related Art

The related art includes gaming devices, on-line gaming, networked interactive gaming, and biometrics.

Gaming Devices

For purposes of this patent, the term "gaming" shall refer to either gambling and/or gaming applications. Gaming devices include games of skill and games of chance. Games of chance include many casino-type gaming devices in which the outcome of the game depends, at least in part, on a randomly generated event. For example, a game of chance may use a random number generator to generate a random or pseudo-random number. The random number may then be compared to a predefined table to determine the outcome of the event. If the random number falls within a certain range of numbers on the table, the player may win a predefined prize. The table may also contain display information that allows the gaming device to generate a display that corresponds to the outcome of the game. The gaming device may present the outcome of the game on a large variety of display devices, such as mechanical spinning reels or video screens.

Games of skill comprises a skill component in which a player combines letters or words (word puzzles), answers questions (trivia), overcomes challenges (video games), competes with other players (networked video games), and the like. Generally, a game of skill is a game requiring a level of skill which does not rely solely on chance. Some games of skill require a high degree of expertise and knowledge and other games of skill require very limited expertise or knowledge.

On-Line Gaming

In June 2001, Nevada signed a bill that could result in Nevada being the first state to offer legalized gambling over the Internet. The new law authorizes state gaming regulators to set up an infrastructure to license and oversee online gaming in Nevada when such gaming becomes legal. Online gaming is a federal issue whose legality is unclear at present.

A variety of technological limitations have been asserted as preventing Congress's endorsement of on-line gaming. These technological limitations are related to the prevention of underage gambling, the control of gambling addiction, and ensure on-line gaming is secure and reliable.

To prevent underage gambling prior art systems and methods use passwords, user IDs, credit cards and "click-through" agreements that ask the player to agree to being of legal gambling age by clicking on a button. Presently, there are no systems and methods to control on-line gambling addiction. With respect to ensuring on-line gaming is secure and reliable, prior art system and methods use various cryptographic techniques such as RSA encryption, digital certificates, or other similar well known cryptographic methods. These cryptographic methods are helpful in ensuring secure communications, however these cryptographic method do not ensure that the individual accessing the on-line game is a valid user.

In view of the prior art systems, a minor or other unauthorized individual may simply needs a user ID and a corresponding password to access a gaming site. The obtaining of a user ID and password is a relatively simple task as this information is generally not modified. Commonly the user ID information is acquired by simply identifying the web site's naming convention for the player. The player password can be easily determined by simply remembering the pattern of keys typed by the player during the log-on procedures or by simply requesting the password from the player as part of a diagnostic procedure. The latter is a trick commonly used by hackers to access a system. The password problem may be overcome by modifying the password on a regular basis, however the player must then remember the modified password and should the player forget the password a new password is mailed. During the mailing process it is common for e-mail to be easily intercepted in cyberspace. Additionally, it is common for unauthorized users to simulate being at a certain location by submitting an IP address that identifies an authorized user.

Therefore, a better system and method for identifying a valid user is needed. Additionally, it would be beneficial to provide a gaming system and method that would prevent underage gambling, is simple to implement, prevents gambling addiction, and provides a higher degree of security and reliability from unauthorized users.

Networked Interactive Gaming

Networked interactive gaming III an open networked environment such as the Internet is well-known. However, interactive gaming in an open network such as the Internet is confined to communicating with other devices using the same TCP/IP protocols. Currently networked interactive gaming systems using the TCP/IP protocol are not configured to communicate with interactive set-top boxes using MPEG protocols.

Networked interactive gaming in an open networked environment using traditional security methods such as secure socket layers and digital certificates are well known. However, networked interactive gaming in an open networked environment using traditional security methods does not prevent gambling from a minor having acquired a parent's user ID and password without the parent's consent.

Networked interactive gaming using LANs and WANs for progressive slot machines having large jackpots are also well-known. However, networked interactive systems using LANs and WANs for progressive slot machines generally exist in a highly secure proprietary network environment. Thus, the creation of a progressive slot machine with a large jackpot in an open network environment is not well known.

Biometrics

A biometric is a measurable psychological and/or behavioral trait that can be captured and subsequently compared with another instance at the time of verification. This definition includes the matching of fingerprints, voice patterns, hand geometry, iris and retina scans, vein patterns and other such methodologies. For purposes of the invention described heretofore, the definition of biometrics also includes signature verification, keystroke patterns and other methodologies weighted towards individual behavior.

Biometric applications for games of skill and games of chance are limited. For example biometric gaming applications are taught in U.S. Pat. No. 6,010,404 granted to Walker et al. teaches a method and apparatus for using player input codes (e.g., numeric, biometric or physical) to affect the outcomes of electronic gambling devices, such as slot machines. Additionally, U.S. Pat. No. 6,142,876 granted to Cumbers teaches a system and method for passively tracking the play of players playing gaming devices such as slot machines. Players provide identification information and facial recognition data is acquired by a digital or video camera. For each player an account file and a file of the facial image data is stored. When the player plays the slot machine, a camera scans the player and acquires facial image data which is compared to stored data to identify the player. Furthermore, U.S. Pat. No. 5,902,983 granted to Crevelt et al. teaches a gaming machine configured to perform EFT transactions which are limited to preset amounts. The patent teaches the use of a finger print imaging device, and retinal scans for verifying a player's identity.

Although biometric applications for gaming applications are known, biometric applications for on-line gaming systems are not known. Furthermore, the managing of biometric information and gaming information in an open network environment are not known. Additionally, the use of biometrics in a gaming system and method to prevent underage gambling and prevent gambling addiction are not known.

SUMMARY

A wireless gaming system comprising a first wireless network access device and a gaming system is described. The first wireless network access device has a plurality of security identification information associated with the first wireless network access device that comprises an Internet Protocol (IP) address. The gaming system is configured to communicate with the first wireless network access device. The gaming system comprises a registration database, a verification system, a video server and a gaming server. The registration database stores registration data associated with each registered user. The verification system is in communication with the wireless network access device and the registration database. The verification system is configured to verify the user is a registered user. The verification system is configured to secure communications with the wireless network access device by verifying the plurality of security information provided by the first wireless network access device including the IP address of the wireless network access device. The video server stores a plurality of images corresponding to a particular game outcome. The gaming server is configured to generate a random game output that associates the random game output with at least one particular game outcome. The gaming server is configured to communicate the images corresponding to the particular game outcome to the first wireless network access device. The gaming server is further configured to be accessible by the wireless network access device after verifying the wireless network device is a secure device, and after verifying the user has registered.

A wireless gaming system that comprises a plurality of wireless network access devices and a gaming system is also described. The verification system in this embodiment comprises a firewall disposed between a gaming server and each wireless network access device. The video server stores a plurality of different animated images, wherein a group of images corresponds to a particular game outcome. The gaming server is configured to generate a random game output that associates the random game output for one of the wireless network access devices with at least one particular game outcome and the corresponding group of animated images. The gaming server is configured to be accessible by the wireless network access device after verifying each wireless network device is a secure device, and after verifying the user has registered. Additionally, an encoder configures the group of animated images as a video stream that is received by each wireless network device.

A wireless gaming method is also described. The wireless gaming method comprises receiving has a plurality of identification information including an Internet Protocol (IP) address. The method then proceeds to communicate the plurality of identification information associated with the wireless network access device to a gaming system. The gaming system comprises a registration database that stores registration data associated with each registered user. The method verifies that the user is a registered user. The method also verifies that the wireless network access device is a secure device by verifying the plurality of identification information associated with the wireless network access device that comprises verifying the IP address. Access to the gaming server is permitted after determining the wireless network device is secure and after determining the user has registered. A random game output is generated at the gaming server. The random game output is associated with a particular game outcome. Images corresponding to a plurality of game outcomes are stored on a video server. The particular game outcome is associated with a plurality of corresponding images and the corresponding images are communicated to the wireless network access device.

A further advantage of the present invention is that it provides a system and method to prevent under'age gambling.

A further advantage of the present invention is that it provides a more secure and reliable and secure gaming system and method.

Another advantage of the present invention is that it provides a system and method for managing biometric information and gaming information in an open network environment.

Another advantage of the present invention is that it permits a plurality of users in a geographically broad area to play the same game.

A further advantage of the present invention is that it provides a pseudo-real time gaming system and method.

Another advantage of the present invention is that it simulates a game of chance such as a slot machine in an on-line environment.

An additional advantage of the present invention is that it provides a networked jackpot.

A networked gaming system that comprises a verification system, a broadband gaming system and a transactional system is described. The verification system operations include ensuring that a user is a registered player by using a biometric input. The broadband gaming system operations include managing and performing at least one game. The transactional system operations include providing oversight for each transaction conducted by the verification system and the broadband gaming system.

A verification system for playing the networked gaming system is described. The networked games include games of chance and games of skill. The verification system communicates with a biometric input module and a network access device to generate a user identification information. The user identification information is compared to information in a registration database. If an acceptable match is made between the user identification information and the information in the registration database, the user is designated as a player. The player then has access to both the broadband gaming system and the transactional system.

A broadband gaming system which is in communication with the verification system is described. The broadband gaming system includes a buffer which stores information about players who desire to play a game. The buffer is operatively coupled to a random number generator that generates a random number for each player in the buffer. A paytable module in communication with the random number generator determines the outcome associated with the random number generator. The paytable also determines which images associated with the outcome for each player. Preferably, the images are stored on a mini video server and then cached in a memory module. The images are intelligently buffered for downstream communications. In its preferred embodiment, a plurality of encoders are operatively coupled to the memory module caching the broadcast video streams. The plurality of encoders encode the broadcast downstream images according the requirements for each network access device. Each encoder is operatively coupled to an encryption module that encrypts the broadcast. A modulation module is operatively coupled to the encryption module and modulates encrypted images for downstream transmission. Each network access device includes a tuner, a demodulation module, and a decryption module permits an image to be viewed by the network access device.

A transactional system and method that ensures secure communications occur in the verification system and the broadband gaming system is described. The transactional system also performs accounting, bonusing, tracking and other such functions. Preferably, the transactional system is capable of receiving a plurality of funds from a financial account and converting them to credits that are used in the broadband gaming system.

The above description sets forth, rather broadly, the more important features of the present invention so that the detailed description of the preferred embodiment that follows may be better understood and contributions of the present invention to the art may be better appreciated. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

Preferred embodiments of the present invention are shown in the accompanying drawings wherein:

FIG. 5 is a table of the data fields in a verification system.

FIG. 6 is a table of the data fields in a broadband gaming system and in a transactional system.

DESCRIPTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Network Access Devices

Referring to FIG. 1a through FIG. 1d there is shown a plurality of illustrative network access devices. Each of the network access devices is configured to be capable of running a gaming application. For illustrative purposes the gaming application shown simulates the spinning reels of a slot machine.

Figure 1A:
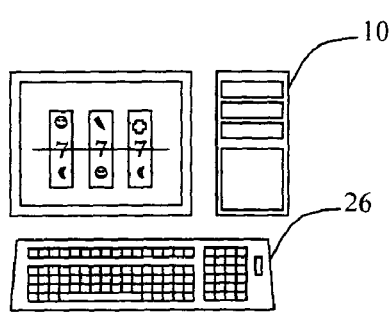
FIG. 1a through FIG. 1d provide diagrams of a plurality of network access devices.
Figure 1B:
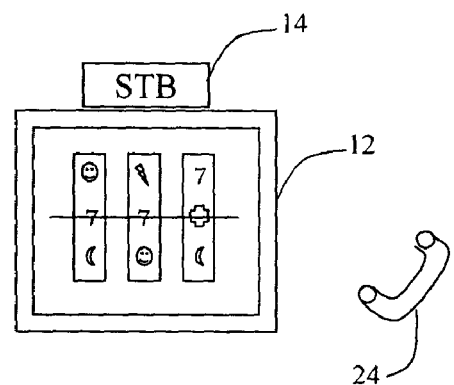
Figure 1C:
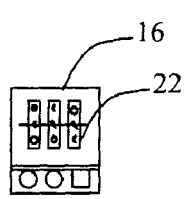
Figure 1D:
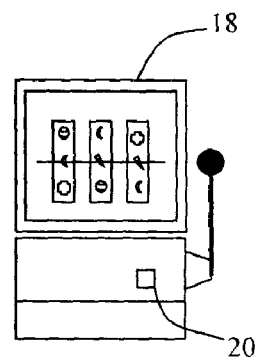

The network access device in FIG. 1a is a personal computer 10 having a network interface card (not shown) that may be operatively coupled to a modem (not shown). Another network access device shown in FIG. 1b includes a television 12 operatively coupled to an interactive set-top box 14 that is operatively coupled to a cable network (not shown). The other network access device shown in FIG. 1c is a wireless device 16 such as a digital phone or personal digital system (PDA) or other such wireless device which is configured to communicate with a network using wireless networking protocols. Yet another network access device is shown in FIG. 1d and includes a gaming terminal 18 such as a slot machine on a casino floor that is operatively coupled to a plurality of other gaming terminals. It shall be appreciated by those skilled in the art of networking that the distinguishing feature between each of these network access devices is the type of communications protocols used by each device to enable communications between similar network access devices.

Each of the network access devices either includes a biometric input module operatively coupled to the network access device or includes a biometric input module communicatively coupled to the network access device. A biometric is a measurable psychological and/or behavioral trait that can be captured and subsequently compared with another instance at the time of verification. This definition includes the matching of fingerprints, voice patterns, hand geometry, iris and retina scans, vein patterns and other such methodologies. For purposes of the invention described heretofore, the definition of biometrics also includes signature verification, keystroke patterns and other methodologies weighted towards individual behavior.

In one illustrative embodiment, the biometric input module is a fingerprint scanner 20 resident on the gaming terminal 18 wherein the biometric input is a fingerprint. In another illustrative embodiment, the biometric input module is the screen 22 of wireless device 16 wherein the screen is configured to receive a biometric input such as a user signature. In yet another illustrative embodiment, the biometric input module is a telephone 24 that is configured to receive a voice pattern from a user prior to engaging communications with the interactive set-top box 14. In yet another illustrative embodiment the biometric input module is a keyboard 26 operatively coupled to computer 10 wherein the user is requested to input a keystroke pattern. An illustrative example of a biometric input module operatively coupled to the network access device is shown in FIG. 1*d* having the fingerprint scanner 20 on the gaming terminal 18. An illustrative example of a biometric input module, e.g. the telephone 24, communicatively coupled to the network access device, e.g. the interactive set-top box 14, is shown in FIG. 1*b*.

The biometric input is used to prevent unauthorized gaming activity and efficiently store credits on the user's behalf. By way of example and not of limitation, unauthorized gaming activity includes preventing underage gaming and prohibiting a player with a history of gambling addiction from playing games of chance. Additionally, player credit's may be stored on a network so that the player does not need to carry coins, paper currency, coupons, credit cards or debits cards to play a game. It shall be appreciated by those skilled in the art having the benefit of this disclosure that different biometric input modules may be used in conjunction with different network access devices.

Gaming System

Figure 2:
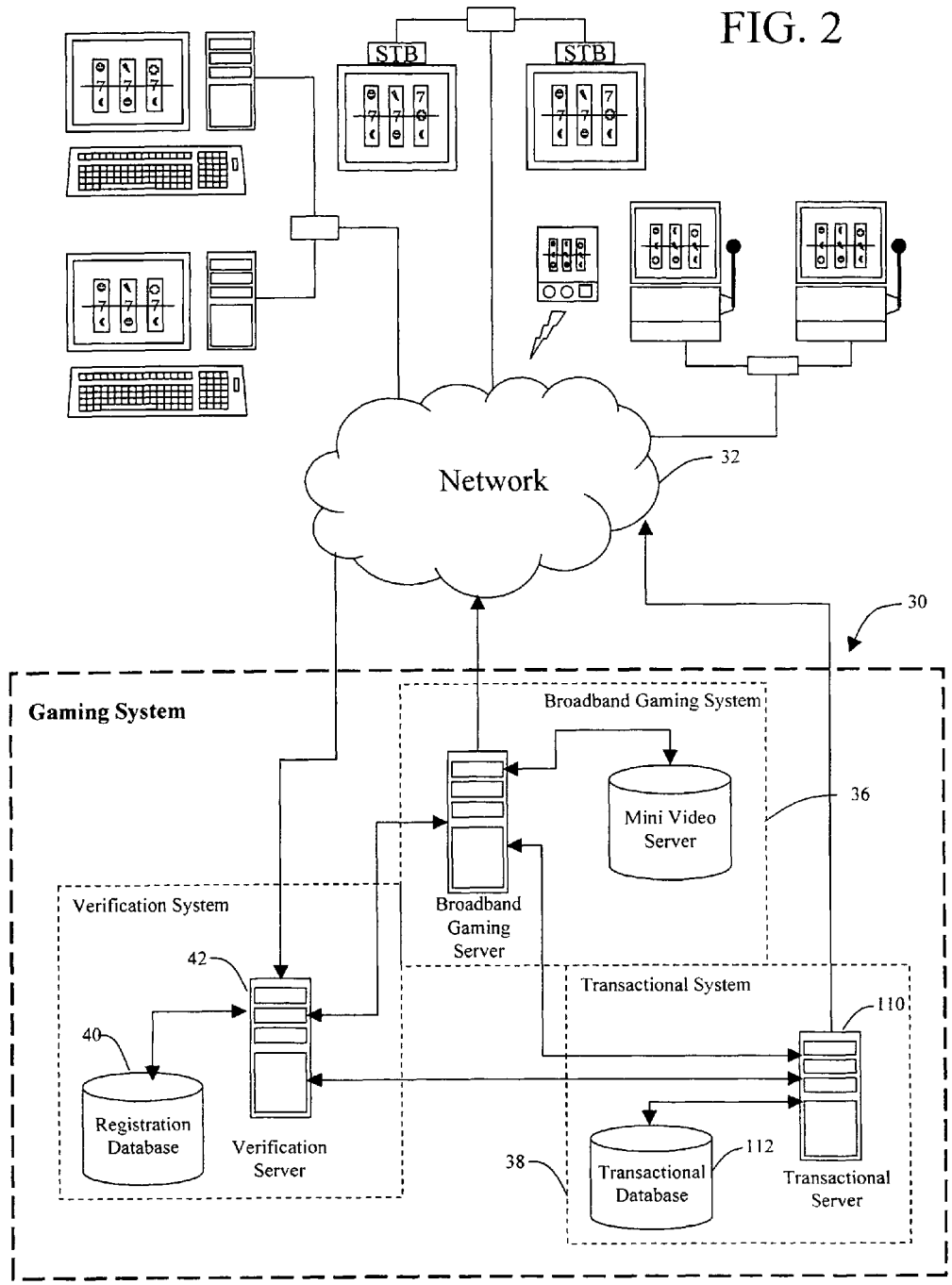
FIG. 2 is a high level diagram of a gaming system networked to a plurality of network access devices.

Referring to FIG. 2 there is shown a high level block diagram of a gaming system 30 in communication with a plurality of network access devices coupled to a network 32. The gaming system includes a verification system 34, a broadband gaming system 36 and a transactional system 38. The verification system 34 verifies that a user operating a network access device is a registered player. The broadband gaming system 36 performs the function of generating a game and broadcasting the game results to each of the network access devices. The transactional system 38 performs a plurality of functions including tracking each transaction performed by both the verification system and the broadband gaming system and conducting electronic fund transfers.

Verification System

The verification system 34 verifies that a user desiring to play the game is a registered player. The verification system 34 communicates with the biometric input module and a network access device to generate user identification information. The user identification information includes information such as cryptographic keys that are necessary to securely identify the network access device. The user identification information also includes media access control (MAC) identification and confirmation of the user Internet Protocol (IP) address. The user identification information is compared to information in a registration database 40 by a verification server 42. If an acceptable match is made between the user identification information and the information in the registration database, the user is designated as a player. The player then has access to either the broadband gaming system 36 or the transactional system 38.

In an alternative embodiment the user identification information is housed in a smart card (not shown) that is communication with the verification system 34. The smart card includes a stored biometric which is used to identify the user as a player. Cryptographic keys are then exchanged between the verification system 34 and the smart card to provide the player access to either the broadband gaming system or the transactional system 38.

Figure 3:
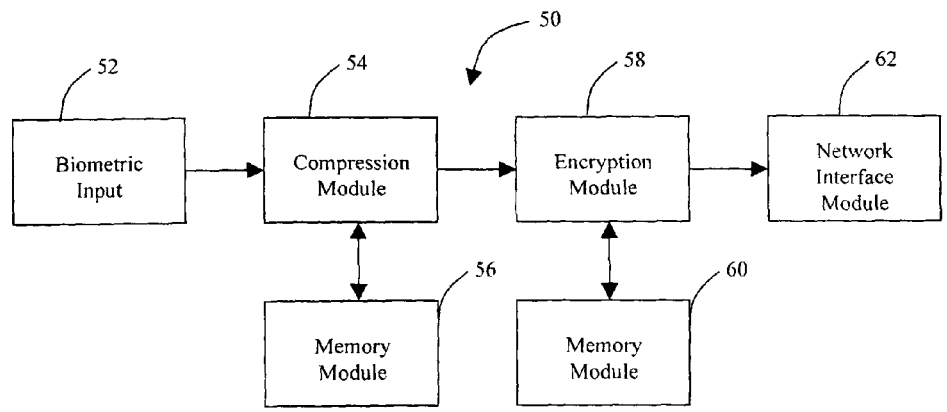
FIG. 3 is a block diagram of an illustrative biometric input module.

Referring to FIG. 3 there is shown an illustrative biometric input module 50. By way of example, the illustrative biometric input module 50 is a fingerprint scanner. It shall be appreciated by those skilled in the art having the benefit of this disclosure that the use of the fingerprint scanner as the illustrative biometric input module is not restrictive. A scanned fingerprint image is collected by the biometric input 52. After the scanned fingerprint image is collected, the fingerprint image is compressed by the compression module 54. A memory module 56 provides fast memory resources for the compression of the fingerprint image. After compression, the fingerprint image is encrypted by the encryption module 58 for downstream transmission. The encryption module 58 also includes a memory module 60 that provides fast memory resources for the encryption of the compressed fingerprint image. An encrypted compressed fingerprint image is then communicated to network 32 (see FIG. 2) using the network interface module 62.

Figure 4:
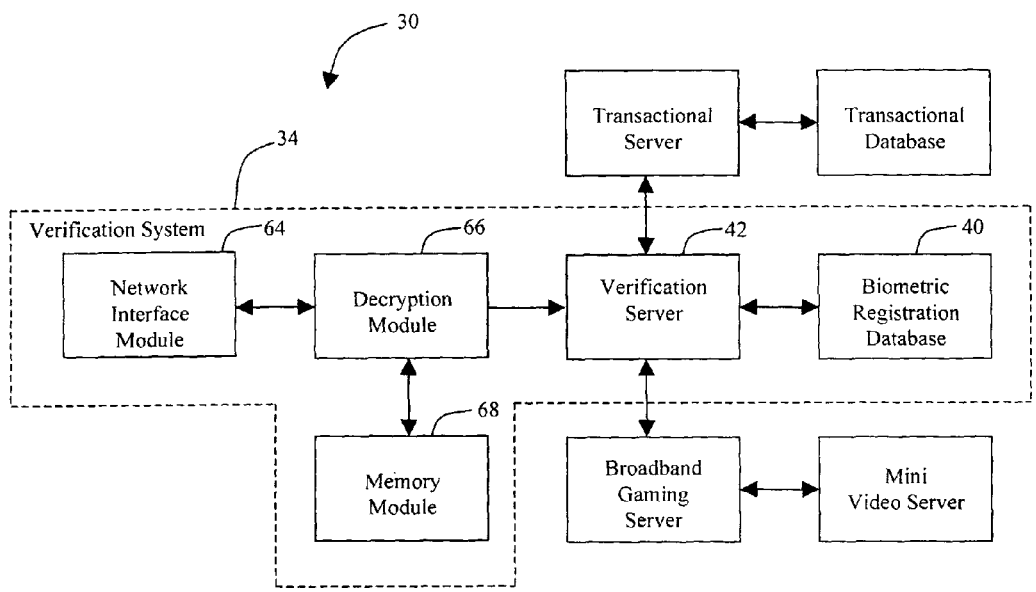
FIG. 4 is a block diagram of a gaming system configured to receive a biometric input from a network access device.

Referring to FIG. 4 there is shown a block diagram of the verification system 34. The verification system is operatively coupled to network 32 with network interface module 64. The network interface module 64 is configured to receive user identification information generated by the network access devices and from the biometric input module. Preferably, the biometric and other user identification information received by the verification system is an encrypted biometric that is decrypted by decryption module 66. A memory module 68 is preferably a fast memory that expedites the decryption process. After decryption the biometric and remaining user identification information is processed by the verification server. It shall be appreciated by those skilled in the art that the verification server 42 may house the network interface module 64, decryption module 66 and the memory module 68. The verification server 42 is also in operative communication with a registration database 40. The verification server 42 performs the function of matching the user identification information collected from the network access device with the player information in the registration database 40. Additionally, the verification server 42 performs the caching functions needed to ensure that once a player has been identified during an initial game, subsequent usage by the same player proceeds quickly.

Preferably, the verification server 42 identifies registered players using a biometric template of the registered player residing on the registration database 40. The registered players are referenced with Personal ID number. When a transaction is undertaken the user firstly calls up the particular template from the registration database 40 by inputting a Personal ID. The Personal ID includes a particular number, user ID, password or other such identification techniques. The inputting of the Personal ID is accomplished with a familiar numeric keypad, keyboard, magstripe card or smart card. The correct template is called and held in memory ready for comparison with the biometric sample provided by the user. A comparison takes place that results in a binary true or false condition as to the identity of the user. The user is in effect claiming an identity by inputting the Personal ID and the system is subsequently verifying that the claim is genuine according to the matching criteria setup within the system.

Referring to FIG. 5 there is shown the registration data fields 70 and user submitted data fields 72. The registration data fields 70 include data fields that comprise the user identification information. The registration data fields include user identification information such as player name, address, user name, password, credit card information, and the date and time of the registration. The player biometric and Personal ID also comprises the user identification information and provides unique information about the player. The Personal ID may be the same as the user name or password. It shall be appreciated by those skilled in the art that some biometric information may be compressed. Furthermore, the user identification information includes data about the network access device and the network connection such as MAC ID, IP addresses, browser type, any cookies resident on the network access device, etc. Finally, the user identification system includes cryptographic keys which are used to encrypt and decrypt the communications between the verification system and each of the network access devices.

The user submitted data fields 72 mirror the registration data fields 70. The user submitted data'fields receive data generated by a user that is attempting to access the broadband gaming system 36. The user submitted information is carefully analyzed to ensure that a valid user is being identified. It is well known that the connection of one network access device to another network access device generates security concerns. Preferably, the present verification system operates using a fast hardware-type firewall that performs a stateful multilayer inspection. In its preferred embodiment the firewall provides packet filtering using a secure protocol such as IPSec. This protocol provides encryption of the data at the packet level as well as at the source address level. Without access to the encryption keys, a potential intruder would have difficulty penetrating the firewall. Additionally, it would be preferable to provide a circuit level gateway and an application level gateway. The circuit level gateway works on the session layer of the OSI model or the TCP layer of the TCP/IP model and monitors TCP handshaking between packets to determine whether a requested session is legitimate. The application level gateway filters data packets at the application layer of the OSI model. A stateful multilayer inspection firewall offers a high level of security, good performance and transparency to end users.

Referring to FIG. 6 there is shown the player data fields 74 that are generated by the broadband gaming system and the transactional system after the user has been verified to be a registered player. The player data fields 74 are used to generate a player matrix which is used as an additional internal security measure. The player data fields 74 include a Player ID that identifies the player, a timestamp that provides the date, time in and time out by the player during the game. Additionally, the type of game, credits played, and credits remaining are monitored. Based on the level of player activity a bonus is provided to the player. Further still the session time for each type of game and the amount played during the session is monitored to better define the type of games the players' like. Transactional information is also monitored and updated, preferably, by the transactional system 38. The transactional information includes credit card information, transaction requests, transaction approval, conversion of monetary funds to credits for playing the game, any transfers of credits for playing the game, and conversions from credits to monetary funds that are credited to the player's financial account. Preferably, communications between the transactional system and the broadband gaming system are conducted in a secure environment using cryptographic keys. Although the use of cryptography within the private network may appear excessive one of the greatest security threats within a private network comes from its own employees. Therefore, it is preferable to use internal firewalls for communications between the broadband gaming system, the transactional system and the verification system.

Broadband Gaming System

Figure 7:
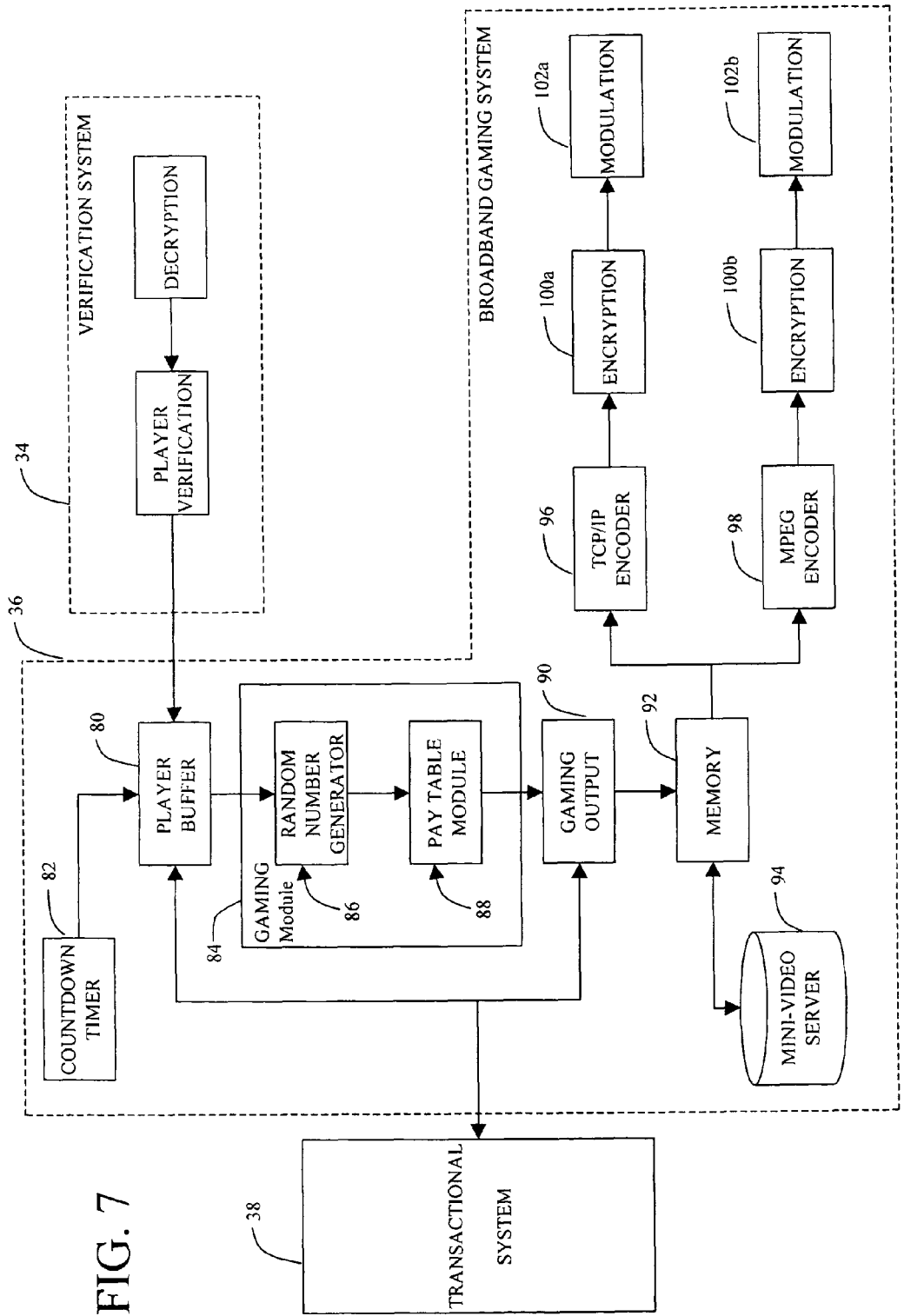
FIG. 7 is a block diagram of a broadband gaming system.

A more detailed drawing of the broadband gaming system is provided in FIG. 7. The dashed boundary FIG. 7 defines the broadband gaming system 36. After player verification is completed at the verification system 34, the broadband gaming system 34 is engaged. The broadband gaming system 34 includes a player buffer 84 configured to receive the players who will be playing the game. The player buffer 84 generates an initial player matrix with player data fields 74.

A countdown timer 82 is coupled to the player buffer 80. Preferably, the countdown timer 82 is also displayed to the player. The countdown timer 82 provides a window of time within which players may join the game. The players that have joined the game before the end of the timing period are stored in the buffer. When the timing period reaches zero the initial player matrix is communicated to the transactional system 38 and to the gaming module 84.

The gaming module 84 provides a game that is played by the plurality of players. The game may include a plurality of different games and the type of game is not restrictive to this invention. Preferably, the gaming module 84 includes at least one random number generator 86 and a paytable module 88.

The random number generator 86 is operatively coupled to the player buffer. The random number generator 86 generates at least one random number that is stored in the player matrix. In one embodiment, at least one random number is generated for the plurality of players playing the game. In an alternative embodiment, at least one random number is generated for each player. In yet another embodiment, a plurality of random numbers are generated that are applied to the plurality of players playing the game. Preferably, the random number generator 86 is a fast hardware module.

A paytable module 88 is operatively coupled to the random number generator 86. The paytable module 88 is a programmable module that determines the type of prize awarded to the player based on the random number generated by the random number generator 86. In one embodiment, the paytable module 88 is a field programmable gate array. Preferably, the paytable module 88 also includes an image ID that is associated with the outcome determined by the paytable module 88.

A gaming output module 90 revises the player matrix to include the outcome for each player. Additionally, the gaming output module 90 groups the players according to the image. ID. Based on the results generated by the gaming module 84, the gaming output module 84 generates a final player matrix that is communicated to the transactional server 38 and to a memory module 92.

Preferably, the memory module 92 has stored a plurality of images in a fast memory by the time the final player matrix is communicated to the memory module 92. In operation, the memory module 92 is enabled before the final matrix is communicated to the memory module 92. By way of example, when the game is engaged the memory module 92 begins the process of finding the applicable images associated with the image IDs in the mini-video server 94 and transferring the images to the fast memory module 92. Thus, when the gaming output is received by the memory, the images are stored in the fast memory module 92. In one embodiment, the memory module 92 then broadcasts the images to encoders 96 and 98. In an alternative embodiment, the memory module 92 is operatively coupled to an intelligent router (not shown) that routes the images to the appropriate encoders 96 and 98.

The appropriate encoder then receives the images and converts them to a format which meets the requirements for the appropriate network access device. By way of example, an IP encoder 96 encodes a plurality of JPEG images for viewing on a conventional web browser, and an MPEG encoder 98 encodes the plurality of JPEG images into an MPEG stream that is viewed on a television via an interactive set-top box.

An encryption module 100*a* and 100*b* operatively coupled to encoder 96 and 98, respectively, then receives the encoded images and encrypts the encoded images in manner well known to those skilled in the art. A modulation module 102*a* and 102*b* is operatively coupled to encryption modules 100*a* and 100b, respectively, then modulates encrypted encoded images for downstream transmission in a manner well known to those skilled in the art.

Preferably, the broadband gaming system occupies one downstream band, i.e. one 6 or 8 MHz band, in the interactive set-top-box environment. In the web based broadcast environment, the broadband gaming system occupies a downstream channel much like a standard streaming media website.

It shall be appreciated by those skilled in the art having the benefit of this disclosure that the broadband gaming system can play more than one game at a time The system may be designed to operate in a multi-tasking mode where more than one game is played at a time. Additionally, the system may be designed to operate in a fast serial mode in which a game is played while the countdown timer is waiting for the next queue to be filled.

Transactional System

Referring back to FIG. 2, there is shown the transactional system 38 which comprises a transactional server 110 and a transactional database 112. The transactional system 38 performs a plurality of functions including tracking each transaction performed by both the verification system and the broadband gaming system. Additionally, the transactional system 38 is configured to authorize and conduct electronic fund transfers. Furthermore, the transactional system 38 performs such operations as player tracking, managing loyalty programs, engaging bonus games, determining bonus prizes and interfacing with accounting programs.

Method for Registering a Player

Figure 8:
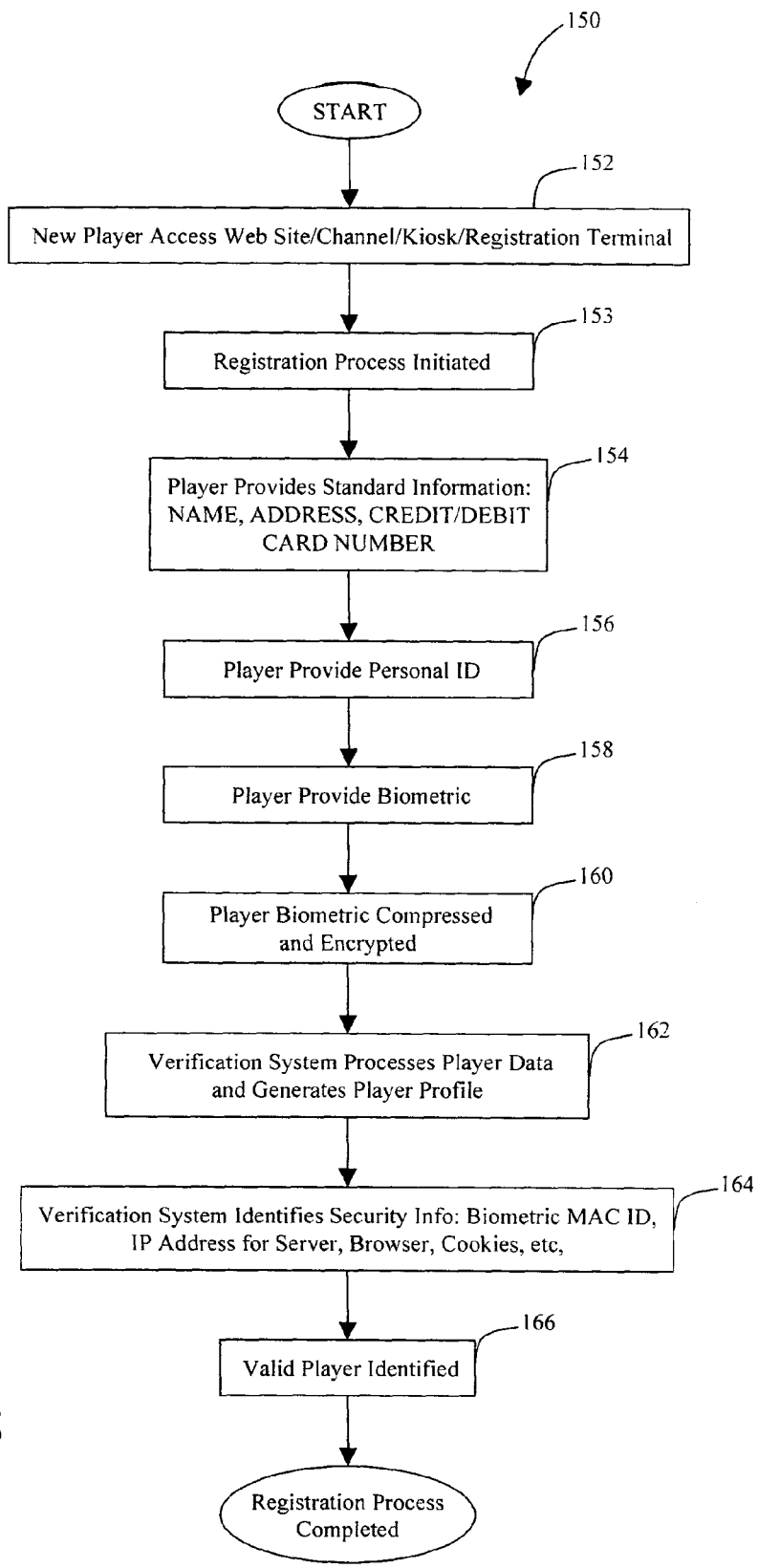
FIG. 8 is a flowchart of the registration method for the gaming system.

Referring to FIG. 8 there is shown a flowchart of the registration method for the gaming system 30. The registration method 150 begins when a prospective player first accesses a website, channel, kiosk or other such registration terminals as described in block 152. The method then proceeds to block 153.

At block 153, the registration process is initiated. By way of example and not of limitation, a registration terminal may provide a hyperlink to a registration window that prompts the prospective player for information. The method then proceeds to block 154.

At block 154, the prospective player provides registration identification information such as name, address, credit card number and other information necessary to create a registration file for the prospective player. The method then proceeds to block 156.

At block 156, the prospective player is prompted for a personal ID. The personal ID may be a user ID, a password, a numeric combination, or any other such identification information. The personal ID is used during the verification process to identify a biometric template for the prospective player. The method then proceeds to block 158.

At block 158, the prospective player submits a biometric to the registration terminal. By way of example and not of limitation the biometric is a fingerprint. Any other biometric may also be used. The method then proceeds to block 160 or 162.

At block 160, the biometric input is compressed and encrypted. It is preferable for certain biometric inputs to compressed such as fingerprint scans, retinal scans and other such scanning techniques. Other biometric inputs such as voice patterns, signatures do not have to be compressed. The process of encrypting biometric inputs is necessary in an open network environment. The process of encrypting may not be necessary on a private proprietary network. Therefore, it shall be appreciated by those skilled in the art having the benefit of this disclosure that the compression and encryption processes in block 160 may not be necessary for every biometric input.

At block 162, the prospective player information is stored in the verification system and a player profile is updated accordingly. Alternatively, the prospective player information is stored on a smart card. The method then proceeds to block 164.

At block 164, security information about the registration terminal is collected. The registration information identifies the registration terminal as being a secure terminal. The registration terminal provides information such as the MAC ID for the biometric input module, the IP address for the server communicating with the registration terminal, and the cryptographic keys associated with the registration terminal. The registration terminal includes the network access devices described in FIG. 1a through FIG. 1d as well as kiosks and other such registration terminals.

At block 166, the prospective player is identified as a registered player and the registration database 40 is updated accordingly. The registration process is broken out into separate components for security purposes. Once a validly registered player is identified by the verification system, the registration process is completed.

Method for Player Verification

Figure 9:
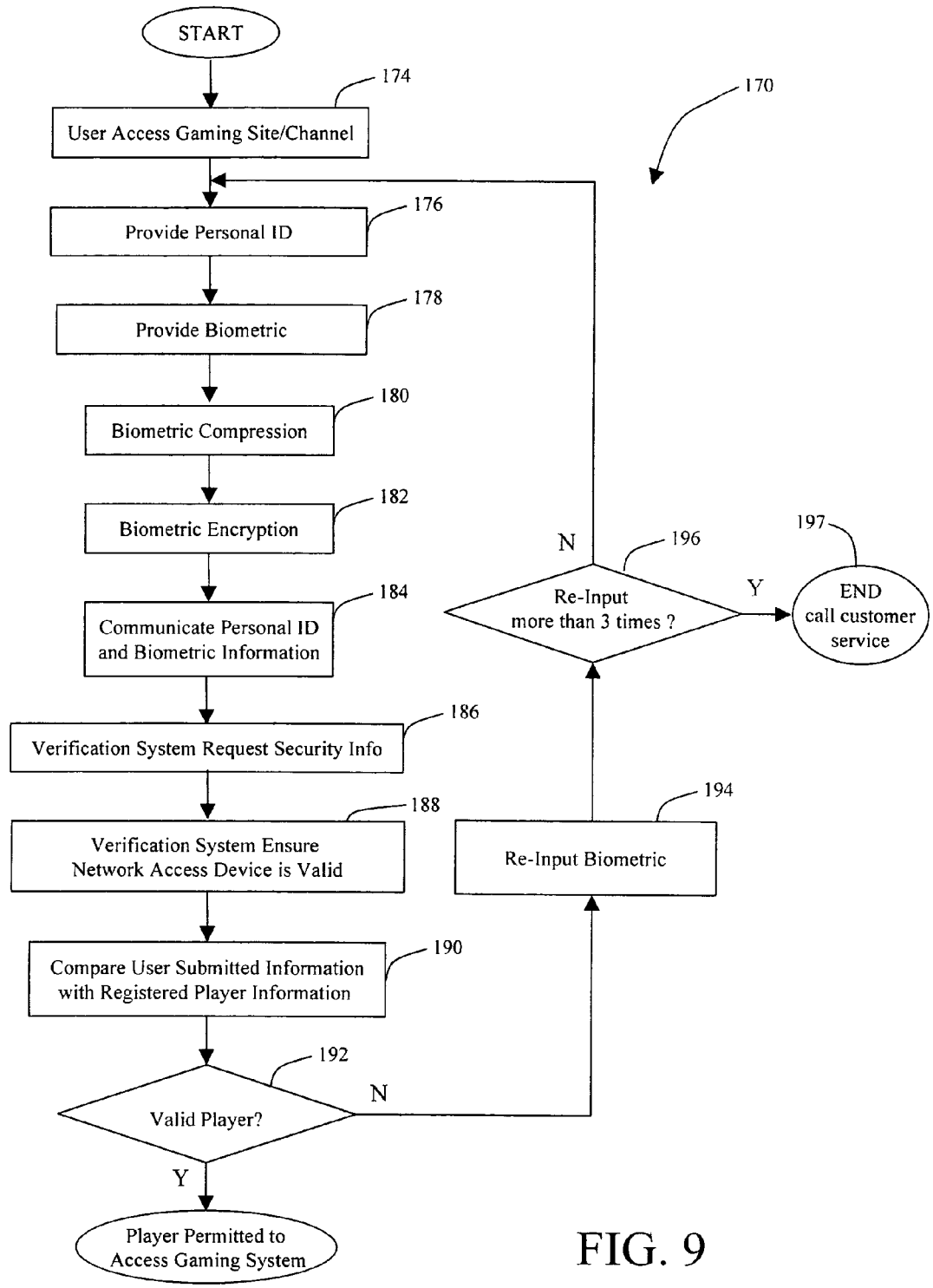
FIG. 9 is a flowchart of the verification method for the gaming system.

Referring to FIG. 9 there is shown a method 170 for player verification used by the verification system 34. The player verification process includes receiving user identification information from a network access device. The method is initiated at block 174 when a user accesses a website or channel displaying the game. The method then proceeds to block 176.

At block 176, the personal ID is provided by the user. The personal ID is used by the verification system to find a biometric template for determining whether the user is a registered player. The method then proceeds to block 178.

At block 178, the biometric input module of the network access device receives a biometric from the user. As previously described the biometric input module can be one of plurality of biometric inputs. Depending on the type of biometric, the biometric may be compressed as described by block 180 and encrypted as described by block 182. At block 184, the biometric and the personal ID is then communicated through a network 32 to the verification system 34. Alternatively, the biometric and Personal ID is communicated to a smart card for verification.

At block 186, the verification system 34 requests security information from the network access devices. The security information identifies the network access devices as being a valid network access device. The method then proceeds to block 188.

At block 188, the verification system 34 processes the security information to ensure that the security, information is generated by the appropriate network access device, and to ensure that the security information has not been compromised. Preferably, the verification system 34 performs a stateful multilayer inspection as described above. The method then proceeds to block 190.

At block 190, the user submitted player information is compared to the registered player information. If a determination is made at decision diamond 192 that the submitted player information is not a valid registered player the method proceeds to block 194. At block 194, the user is requested to re-input the biometric. If the biometric is input more than three times, as provided by decision diamond 196, the user is requested to contact customer service.

If a match is found at decision diamond 192 between the user submitted information and the registered player information, the user is identified as a valid player then the player proceeds to the broadband gaming system 36.

Method for Operation of Broadband Gaming System

Figure 10:
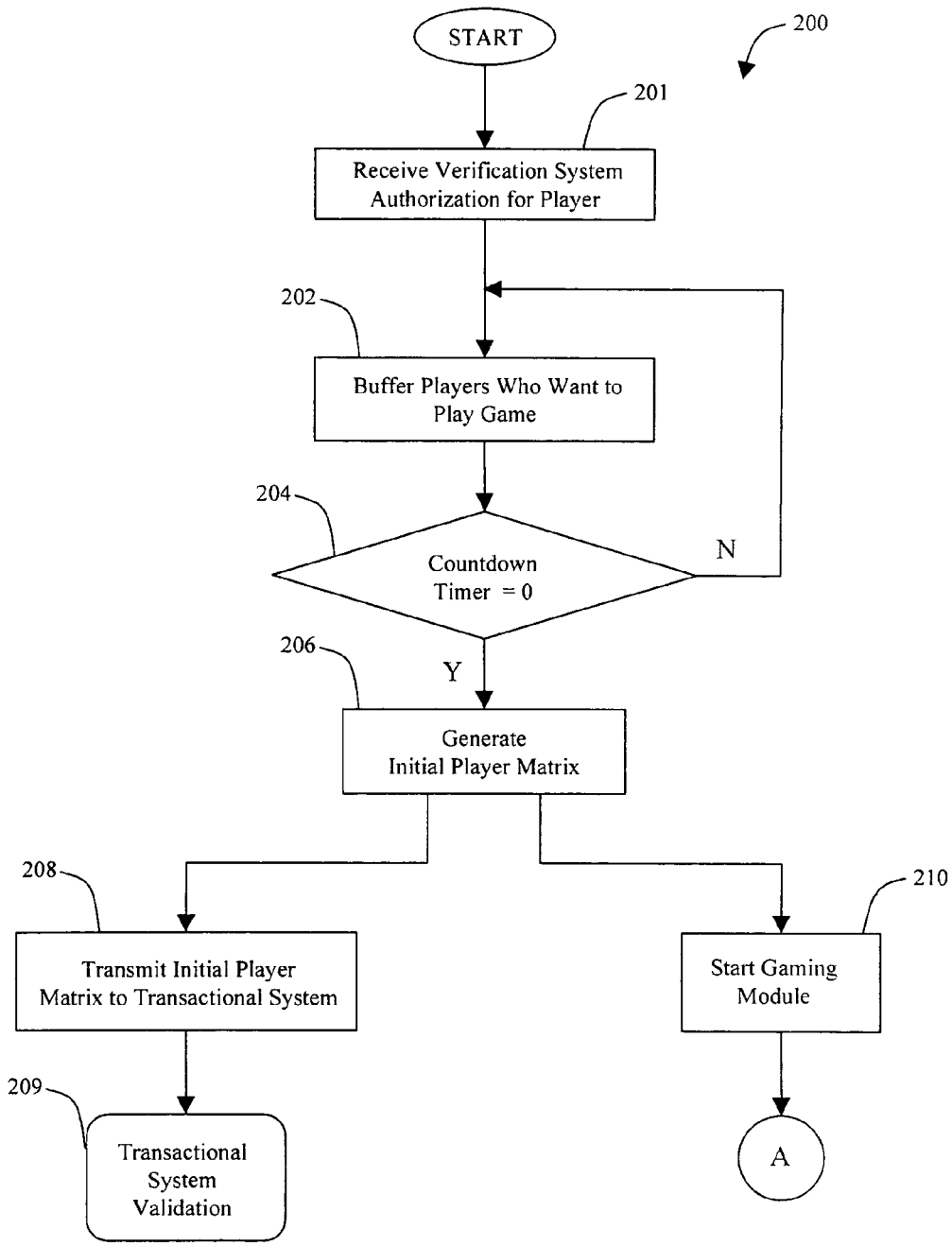
FIG. 10 is a flowchart of the information processed by the gaming system.
Figure 11:
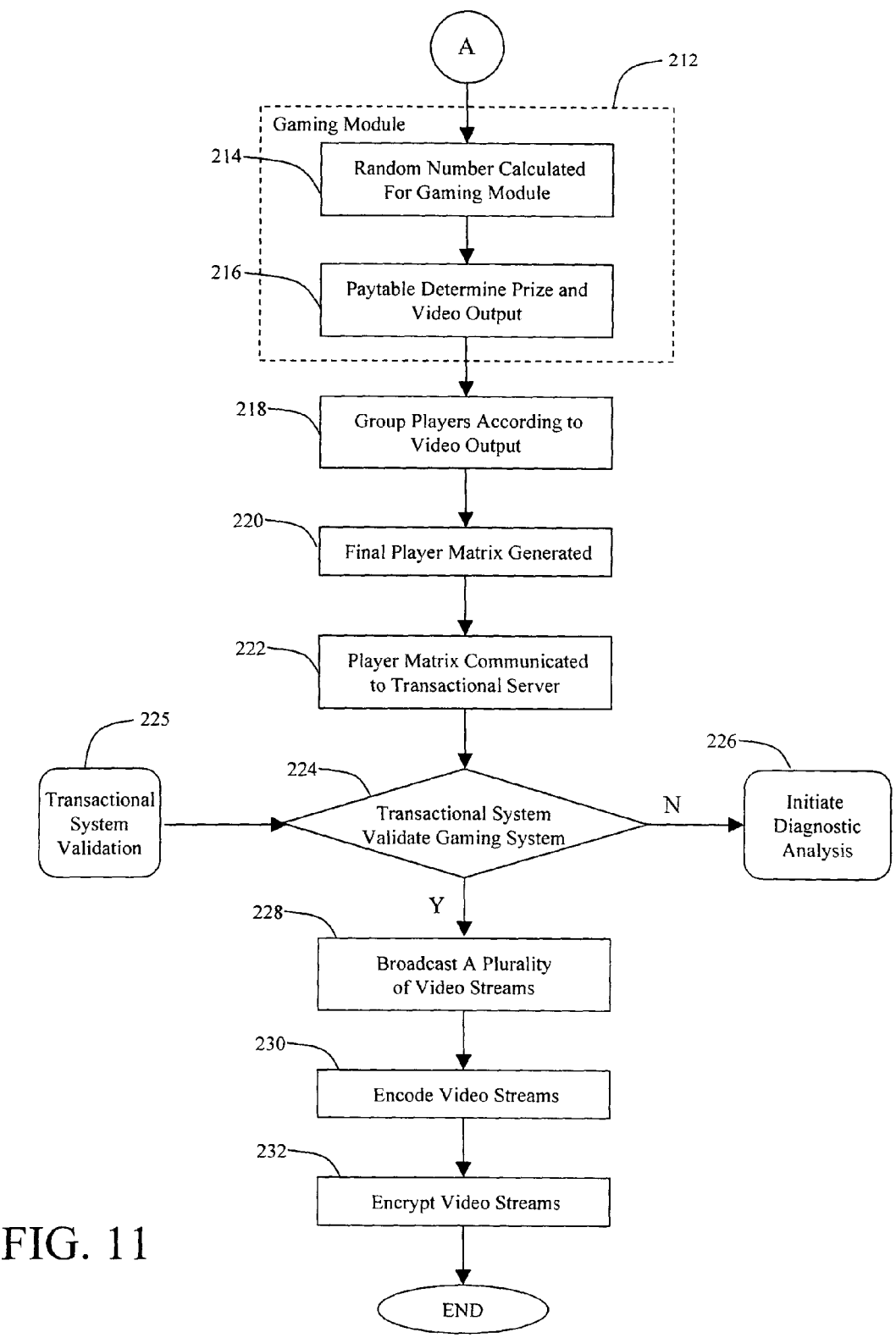
FIG. 11 is a continuation of the flowchart of the information processed by the gaming system in FIG. 10.

Referring to FIG. 10 and FIG. 11 there is shown a flowchart 200 of the information processed by the broadband gaming system 34. The process is engaged by performing the verification process in which the verification system identifies a player as in block 201. After the verification process has been completed the method proceeds to block 202.

At block 202, the players who desire to play a particular game are stored in a buffer until the particular game is engaged. The method then proceeds to decision diamond 204.

At decision diamond 204, the countdown timer 82 determines if the period during which the game is open has been closed. If the game remains open, additional players may be received by the broadband gaming system. If the game games is closed because the period during which the game is open has expired, then the method proceeds to block 206.

At block 206, the initial player matrix described above is generated. The initial player matrix includes information about the player, the type of game, and other such information about the game as described by the player data fields 74 shown in FIG. 6. The initial player matrix is then communicated to block 208 which transmits initial player matrix to the transactional system for validation. Additionally, the initial player matrix is communicated to the next block 210 in the broadband gaming system which starts the gaming module.

At block 210, the initial player matrix is received by the gaming module 84 and the gaming module 84 is engaged. At a minimum the gaming module 84 comprises a random number generator 86 and a paytable module 88. The random number generator generates at least one random number that is used during the game. The paytable module 88 is used to determine the prize associated with the at least one random number.

Referring to FIG. 11, a continuation of the broadband gaming system method is shown. By way of example, the gaming module may comprise a plurality of different random number generators. The blocks 214 and 216 describe the processes performed by a random number generator and a paytable module, respectively. The random number generator 86 of block 214 determines the winning combination of numbers for the game. At block 216, the paytable module 88 is used to determine the prize awarded to the player. Preferably, the paytable module 88 is also configured to provide image IDs that identify the images associated with the prize. Preferably, the paytable module 88 is resident in both the broadband gaming system and the transactional system. The purpose for this redundancy is as a security check for output generated by the gaming module. The method then proceeds to block 218.

At block 218 the player outputs with the same image IDs are grouped together. The grouping process is performed to simplify the broadcasting of the images to the plurality of players. By grouping the players according to the same image ID and having identified the network access device used by the player, a dynamic broadcasting method is created which occupies minimal downstream bandwidth. The method then proceeds to block 220.

At block 220 a final player matrix is completed. The final player matrix includes the same data fields as the initial player matrix. Additionally, the final player matrix includes the random number output and the paytable output. The final player matrix is then communicated to the transactional system as described in block 222. The method then proceeds to decision diamond 224.

At decision diamond 224, a validation procedure is conducted. The validation procedure essentially compares the transactional system's reverse calculation of the random numbers with the random numbers generated by the gaming module. If the random numbers in the transactional system are not the same or similar to the random numbers generated by the random number generator, a system failure or security breach is detected. If a security breach or system failure is detected, the method then proceeds to process block 226, which initiates diagnostic procedures. If the random numbers match, then the method proceeds to block 228.

At block 228, the plurality of images are broadcast. The images are preferably broadcast along one downstream channel for each network access device. However, traffic considerations may require the use of a plurality of downstream channels. By way of example, for DOCSIS and DSL type downstream transmissions, the streaming video preferably occupies a portion of the bandwidth available for a cable modem or DSL modem, respectively. In an alternative example, for an interactive set-top box environment, the downstream channel preferably occupies one 6 MHz or 8 MHz band or a portion of the 6 MHz or 8 MHz band. The method then proceeds to the next block 230.

At block 230, the broadcast images are encoded for downstream transmission. It shall be appreciated by those skilled in the art having the benefit of this disclosure that downstream transmission systems are well known and can be easily integrated into the systems and method described in this patent. The method then proceeds to block 232.

At block 232, the broadcast images are encrypted for downstream transmission. The purpose for downstream encryption is to prevent unauthorized access to the downstream signal. It shall be appreciated by those skilled in the art that various secure systems and methods for downstream transmission of images are well known.

It shall be appreciated by those skilled in the art having the benefit of this disclosure that a plurality of games may be played simultaneously. The games may be played in a distributed/parallel manner or in serial manner.

An Illustrative Game

An illustrative game is described to show how the system and method described above operates. The illustrative game described herein is a progressive slot machine. It is well-known that in the United States many states have legalized lottery games even though other games of chance such as progressive slot machines have not been legalized. It is also well-known that in casino gaming floors the most popular games are progressive slot machines. The present illustrative game operates on the system and method described above and provides an output similar to a progressive slot machine with a lottery type input.

The illustrative game includes first having a player provide a plurality of letters or numbers that are either generated by the player or are selected in a random manner. The random number generator of the gaming module is then engaged and a gaming module random number is generated. Preferably, the order that the random numbers were generated is used to determine the prize awarded to the player. A programmed paytable is then used to compare the player selected numbers to the gaming module random numbers according to the rules programmed into the paytable module. Based on the results of this comparison a prize is awarded to the player. An image ID is associated with the prize awarded. The plurality of players are then grouped according to their respective image IDs. A broadcast stream for the plurality of images associated with each image ID is broadcast to each player.

A more concrete example includes having a player select a plurality of numbers, such as the numbers below:

25 35 8 15 42

The random number generator of the gaming module is then engaged. By way of example the random number results are:

56 2 3 8 42

The paytable module is then programmed to interpret the random numbers generating by the gaming module according to the following illustrative rules:

1. If a match between one number is achieved, then a prize of 1× the initial bet credit is awarded and an image ID XQ23-1396 is used. Image ID XQ231396 is an animated plurality of images representing three cherries.
2. If a match between one number at the same location is achieved, then a prize of 2× the initial bet credit is awarded and an image ID XQ23-1397 is used. Image ID XQ23-1397 is an animated plurality of images representing four cherries.
3. If a match between a first number is achieved and a match between a second number is achieved, then a prize of 5× the initial credit is awarded and an image ID XQ23-1998 is used Image ID XQ23-1998 is an animated plurality of images representing 3 oranges.
4. If a match between a first number at the same location is achieved and a match between a second number is achieved, than a prize of 7× the initial credit is awarded and an image ID XQ23-1999 is used. Image ID XQ23-1999 is an animated plurality of images representing 4 oranges.

Thus, for the illustrative example provided above, the player having selected the numbers: 23, 35, 8, 15 and 42 is entitled to a prize of 7× the initial credit for a random number: 56, 2, 3, 8, and 42. The associated images displayed on the network access device is an animated plurality of images representing 4 oranges.

The scope of the invention should be determined by the appended claims and their legal equivalents rather than by the examples given.

What is claimed is:

1. A wireless gaming system, comprising:
   a first wireless network access device having a plurality of security identification information associated with the first wireless network access device that comprises an Internet Protocol (IP) address;
   a gaming system that is configured to communicate with the first wireless network access device, the gaming system comprising,
      a registration database that stores registration data associated with each registered user;
      a verification system in communication with the wireless network access device and the registration database, said verification system configured to verify the user is a registered user;
      said verification system comprising a firewall disposed between a gaming server and the wireless network access device;
      said verification system further configured to secure communications with the first wireless network access device by verifying the plurality of security information associated with the first wireless network access device comprising a media access control (MAC) address and an IP address associated with the wireless network access device;
      a video server that stores a plurality of different animated images corresponding to at least one particular game outcome;
      the gaming server configured to generate a random game output that associates the random game output with at least one particular game outcome, said gaming server configured to communicate the plurality of images corresponding to the particular game outcome to the first wireless network access device, said gaming server configured to be accessible by the wireless network access device after verifying the wireless network device is a secure device, and after verifying the user has registered; and
      a video encoder that configures the plurality of animated images as a video stream that is received by the wireless network device.

2. The wireless gaming system of claim 1 further comprising a transactional system configured to monitor transactions between the wireless network access device and the gaming system.

3. The wireless gaming system of claim 1 wherein said first wireless network device is a digital phone.

4. The wireless gaming system of claim 1 wherein said first wireless network device is a personal digital assistant (PDA).

5. The wireless gaming system of claim 1 wherein the verification system is configured to verify the user is a registered user by comparing a user ID and password to information in the registration database.

6. The wireless gaming system of claim 1 wherein the verification system is configured to verify the user is a registered user by authenticating a smart card.

7. A wireless gaming system, comprising:
   a plurality of wireless network access devices, each having a plurality of security identification information associated therewith that comprises an Internet Protocol (IP) address; and
   a gaming system that is configured to communicate with each wireless network access device, the gaming system comprising,
      a registration database that stores registration data associated with each registered user;
      a verification system in communication with each wireless network access device and the registration database, said verification system configured to verify the user of each wireless network access device is a registered user;
      said verification system comprising a firewall disposed between a gaming server and each wireless network access device, said verification system configured to secure communications with each wireless network access device by verifying the plurality of identification information associated with each wireless network access device comprising a MAC address and an IP address associated with each wireless network access device;
      a video server that stores a plurality of different animated images, wherein a group of images corresponds to a particular game outcome;
      the gaming server configured to generate a random game output that associates the random game output for one of the wireless network access devices with at least one particular game outcome and the corresponding group of animated images and to communicate the group of animated images to the wireless network access device, said gaming server configured to be accessible by the wireless network access device after verifying the wireless network device is a secure device, and after verifying the user has registered; and
      a video encoder that configures the group of animated images as a video stream that is received by each wireless network device.

8. The wireless gaming system of claim 7 wherein the verification system is configured to verify the user is a registered user by comparing a user ID and password to information in the registration database.

9. The wireless gaming system of claim 7 wherein the verification system is configured to verify the user is a registered user by authenticating a smart card.

10. The wireless gaming system of claim 7 wherein the plurality of identification information associated with each wireless network access device comprises cryptographic keys, which are used to encrypt and decrypt communications between the verification system and each of the network access devices.

11. A wireless gaming method, comprising:
receiving a plurality of identification information from a wireless network access device, the information including an Internet Protocol (IP) address associated with the wireless network access device;
communicating the plurality of identification information associated with the wireless network access device to a gaming system, the gaming system comprising a registration database that stores registration data associated with a registered user;
verifying a user is a registered user;
verifying the wireless network access device is a secure device by verifying the plurality of identification information associated with the wireless network access device including verifying the IP address and the MAC address, wherein a firewall is disposed between a gaming server and the wireless network access device;
permitting access to the gaming server after determining the wireless network device is secure and after determining the user has registered;
generating a random game output at the gaming server;
associating the random game output with a particular game outcome;
storing a plurality of different animated images corresponding to a plurality of game outcomes on a video server;
associating the particular game outcome with a plurality of corresponding animated images;
configuring the plurality of animated images as a video stream with a video encoder; and
communicating the plurality of corresponding images from the gaming server to the wireless network access device.

12. The wireless gaming method of claim 11 further comprising monitoring transactions between the wireless network access device and the gaming server.

13. The wireless gaming method of claim 11 further comprising verifying the user is a registered user by comparing a user ID and password to information in the registration database.

14. The wireless gaming method of claim 11 further comprising verifying the user is a registered user by authenticating a smart card.

15. The wireless gaming system of claim 1 wherein the gaming server further comprises a paytable module configured to associate the random game output with the particular game outcome.

16. The wireless gaming system of claim 15 wherein the paytable module is configured to determine the plurality of images corresponding to the particular game outcome.

17. The wireless gaming system of claim 7 wherein the gaming server further comprises a paytable module configured to associate the random game output with the particular game outcome.

18. The wireless gaming system of claim 17 wherein the paytable module is configured to determine the plurality of images corresponding to the particular game outcome.

19. The wireless gaming method of claim 11 wherein associating the particular game outcome with a plurality of corresponding images includes a paytable module configured to associate the random game output with the particular game outcome, the paytable module configured to determine the plurality of images corresponding to the particular game outcome.

20. The wireless gaming system of claim 1 wherein the gaming server is further configured to communicate the plurality of images to the first wireless network access device by way of a downstream transmission.

21. The wireless gaming system of claim 7 wherein the gaming server is further configured to communicate the random game output by way of a downstream transmission to one of the wireless access devices.

22. The wireless gaming method of claim 11 further comprising transmitting the random game output to the wireless network device from the gaming server via a downstream transmission.

* * * * *

UNITED STATES PATENT AND TRADEMARK OFFICE
CERTIFICATE OF CORRECTION

| | | |
|---|---|---|
| PATENT NO. | : 8,403,755 B2 | Page 1 of 1 |
| APPLICATION NO. | : 10/681034 | |
| DATED | : March 26, 2013 | |
| INVENTOR(S) | : Michael A. Kerr | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 647 days.

Signed and Sealed this
Eleventh Day of November, 2014

Michelle K. Lee
*Deputy Director of the United States Patent and Trademark Office*